United States Patent
Garcia et al.

(10) Patent No.: US 7,116,421 B2
(45) Date of Patent: Oct. 3, 2006

(54) DEVICE AND METHOD FOR DIFFERENTIAL SENSING OF HYDROGEN GAS USING THERMOABSORPTANCE OR THERMOREFLECTANCE

(76) Inventors: Jose Agustin Garcia, 14 Blakley Avenue, Toronto, Ontario (CA) M6N 3Y5; Andreas Mandelis, 3 Scarborough Heights Blvd, Toronto, Ontario (CA) M1M 2V3; Chinhua Wang, Apt. #213, 790 Springland Dr., Ottawa, Ont. (CA) K1V 6L7

(*) Notice: Subject to any disclaimer, the term of this patent is extended or adjusted under 35 U.S.C. 154(b) by 107 days.

(21) Appl. No.: 10/384,598

(22) Filed: Mar. 11, 2003

(65) Prior Publication Data

US 2004/0017571 A1 Jan. 29, 2004

Related U.S. Application Data

(60) Provisional application No. 60/364,099, filed on Mar. 15, 2002.

(51) Int. Cl.
*G01N 21/00* (2006.01)
(52) U.S. Cl. .............. 356/437; 73/31.06; 422/83; 422/88; 250/227.27
(58) Field of Classification Search ........ 356/432–440, 356/445, 448; 385/12; 250/227.19, 227.27; 422/86, 88, 91; 204/424–426; 73/31.06
See application file for complete search history.

(56) References Cited

U.S. PATENT DOCUMENTS

| 4,661,320 | A | * | 4/1987 | Ito et al. ................. 422/86 |
| 6,006,582 | A | * | 12/1999 | Bhandari et al. ........ 73/23.2 |
| 6,519,041 | B1 | * | 2/2003 | Berthold ................. 356/477 |
| 6,535,658 | B1 | * | 3/2003 | Mendoza et al. ......... 385/12 |
| 6,596,236 | B1 | * | 7/2003 | DiMeo et al. ............ 422/88 |
| RE38,344 | E | * | 12/2003 | Kuriakose et al. ....... 73/23.4 |
| 6,734,975 | B1 | * | 5/2004 | Eblen et al. ............ 356/445 |
| 2003/0024813 | A1 | * | 2/2003 | Taniguchi ............... 204/424 |

FOREIGN PATENT DOCUMENTS

JP 2004-354163 * 12/2004

* cited by examiner

*Primary Examiner*—Hoa Q. Pham

(57) ABSTRACT

A hydrogen sensor, useful for trace hydrogen gas detection. The sensor involves providing a gas sample, generating modulated optical excitation sources, bringing the optical excitation source to the side of a metalized thin pyroelectric film, and detecting via a lock-in amplifier circuit the coherent differential signal resulting from thermoreflectance and thermoabsorptance changes in the film when exposed to hydrogen gas.

33 Claims, 6 Drawing Sheets

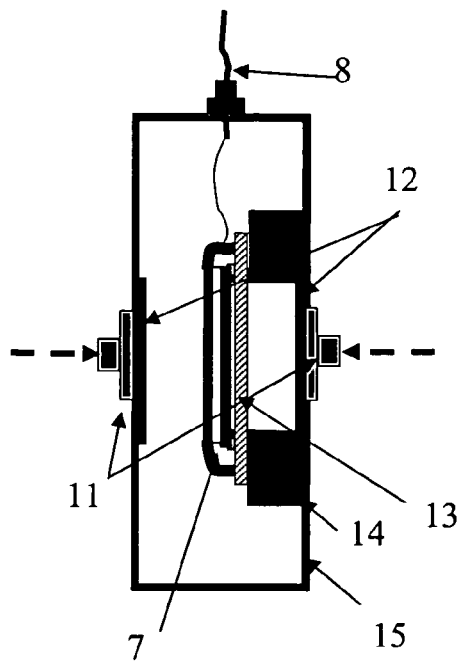
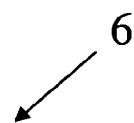
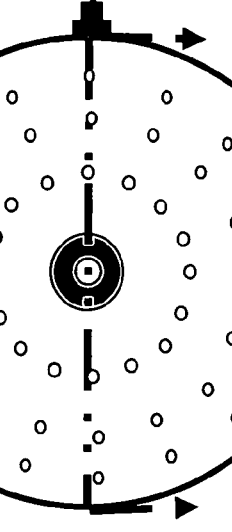
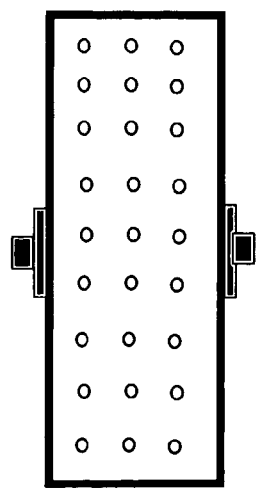
FIG. 2A
FIG. 2C
FIG. 2B

DEVICE AND METHOD FOR DIFFERENTIAL SENSING OF HYDROGEN GAS USING THERMOABSORPTANCE OR THERMOREFLECTANCE

We claim the benefit of the Priority date Mar. 15, 2002 as per Provisional Patent Application No. 60/364,099.

TECHNICAL FIELD

The present invention relates to differential hydrogen gas detection instrumentation based on thermoreflectance and thermoabsorptance, and on polarization-dependant reflectance.

BACKGROUND OF THE INVENTION

The large variety of hydrogen gas sensors are based on electronic devices and use of palladium as the active membrane. Reports on the most common hydrogen sensors of this type include: Palladium (Pd)-gated MOS transistors and Pd-gate metal-insulator-semiconductor (MIS) sensors (see K. I. Lundstrom, M. S. Shivaraman, C. M. Svensson. J. Appl. Phys. 46, 3876, 1975); Pd—CdS and Pd-insulator Schottky barrier diodes (see M. C. Steele and B. A. MacIver, Appl. Phys. Lett. 28, 687, 1976); the double metal-gate MISFET (see T. Yamamoto, and M. Morimoto, Appl. Phys. Lett., 20, 269, 1976) and the insulator gate field-effect transistor, IGFET, (see T. L. Poteat, and B. Lalevic, IEEE Trans. Electron Devices ED-29, 123, 1982); surface acoustic wave based sensors, SAW, (see A. D'Amico, A. Palma, and E. Verona, Appl. Phys. Lett. 41, 300, 1982); optical fiber sensors (see M. A. Buttler, Sensors and Actuators B 22, 155, 1994; A. Mandelis and J. A. Garcia, Sensors and Actuators B 49, 258, 1998; John W. Berthold, U.S. Pat. No. 6,519,041; Mendoza et al., U.S. Pat. No. 6,535,658; J. Mitsubishi, JP-2004-354, 163); optical interferometric sensor (see A. Bearzotti, C. Caliendo, E. Verona, and A. D'Amico, Sensors and Actuators B 7, 685, 1992), surface spectroscopic sensors (Eblen et al., U.S. Pat. No. 6,734,975); rare earth metal thin film sensors (Bhandari et al., U.S. Pat. No. 6,006,582; DiMeo et al., U.S. Pat. No. 6,596,236); electrochemical sensors (N. Taniguchi, US-2003/0024813; Kuriakose et al., US-RE38,344); catalytic sensors (Ito et al., U.S. Pat. No. 4,661,320); and photopyroelectric sensors (see A. Mandelis and C. Christofides, Sensors and Actuators B 2, 79, 1990; C. Christofides and A. Mandelis, Rev. Sci. Instr. 64, 3563, 1993).

Palladium (Pd) has proven to be a particularly suitable material due to its capability to absorb large amounts of hydrogen to form a hydride and to desorb reversibly. Taken together with polyvinylidene (di)fluoride (PVDF) as a photopyroelectric (PPE) sensor, it provides a way of detecting the presence of hydrogen due to the changes in electronic properties (pyroelectric coefficient of the OVDF and work function of Pd) and optical properties (surface absorptance and reflectivity), which result in a pyroelectric phenomenon that poled PVDF files ($\beta$ phase) generates a voltage difference in the direction of poling between the two metalized electrode surfaces which sandwich the pyroelectric film when a temperature change is induced within the pyroelectric layer.

Previous work has focused on the fabrication of Pd-coated polyvinylidene (di)fluoride (Pd—PVDF) thin film photopyroelectric (PPE) sensors (see A. Mandelis and C. Christofides, Sensors and Actuators B 2, 79, 1990; C. Christofides and A. Mandelis, Rev. Sci. Instr. 64, 3563, 1993). A sensor that detected down to 0.075% hydrogen concentration in a flowing H2+N2 mixture by employing two detectors (one active and one reference) and two signal processing electronics (see A. Mandelis and C. Christofides, Sensors and Actuators B 2, 79, 1990). Since then efforts have been made to simplify the detection system by employing either a purely optical method (see A. Mandelis and J. A. Garcia, Sensors and Actuators B 49, 258, 1998) or by use of a single detector (see C. Christofides and A. Mandelis, Rev. Sci. Instrum. 64, 3563, 1993). However the detectivity in these cases was compromised by a large baseline signal and noise introduced by the intensity fluctuations of the incident light.

More recently a PPE interferometric sensor has been reported (see C. Wang, A. Mandelis and J. A. Garcia, Sensors and Actuators B 60, 228, 1999). In this case a He—Ne laser split into two beams and modulated out-of-phase with a mechanical chopper was used to generate the PPE signals. This system is bulky and not practical for portable hydrogen gas monitoring systems. There is a need for a device simpler in its hardware configuration and portable in deployment.

SUMMARY OF THE INVENTION

An apparatus for detecting hydrogen gas including a radiation source for generating at least two optical signals of the same frequency; a sensor head, comprising a pyroelectric film, the pyroelectric film with a first side coated with a hydrogen-sensitive metallic substance and a second side coated with a hydrogen-insensitive metallic substance; a remote optical signal transmission element for delivering an optical signal to the two sides, thereby generating a zero voltage across the two sides in the absence of hydrogen gas and a non-zero voltage in the presence of hydrogen gas; and a circuit element electronically connected to the two sides for monitoring the voltage generated.

In a variation, the apparatus includes a photoelastic modulator for modulating the polarizations of the optical signal delivered to the sensor head, which comprises a photoreflecting film, the photoreflecting film including a sensor surface coated with a photoreflecting metallic substance.

BRIEF DESCRIPTION OF THE DRAWINGS

The methods of the present invention described reference the accompanying drawings in which:

FIG. 2 illustrates a schematic diagram of the components in the gas sensing head of one embodiment of the device;

DETAILED DESCRIPTION OF THE INVENTION

Thermoabsorptance Hydrogen Sensing

There is provided a hydrogen sensor, useful for trace hydrogen gas detection. The sensor comprises a metalized thin pyroelectric film, PVDF sputter-coated with palladium on one side and an electrically conducting material inert to hydrogen, such as Ni—Al alloy, on the opposite surface. A metal such as palladium works well but this invention may also work with any other hydrogen selective and electrical conducting coating instead of the Pd. Any other electrical conducting inert to hydrogen, for the opposite side, or electrical conducting polymers as well. A rigged pyroelectric element, such as PZT or $LiNbO_3$ disk can be substituted for PVDF within the domain of this disclosure. The basic criteria are that it must be able to adsorb and absorb $H_2$ which then will have to change its optical properties and perhaps the molecular/electronic properties of the substrate (PVDF). Also, the coatings have to be electrical conductors to generate an external electrical voltage which will be detectable by common types of electrical/electronic detectors, such as lock-in amplifiers.

Figure 1:
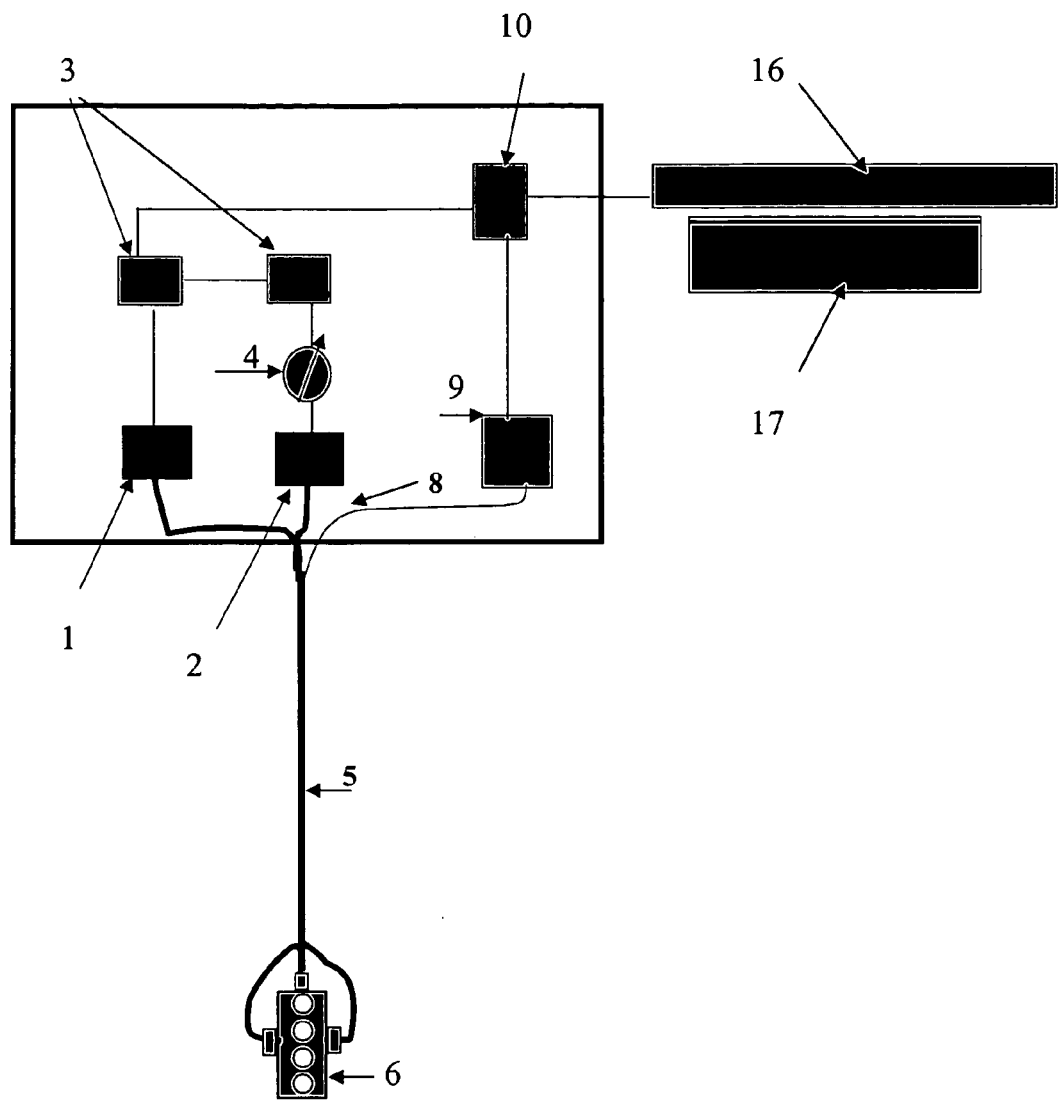
FIG. 1 illustrates a schematic diagram of one embodiment of the present invention used for measuring hydrogen gas traces using changes in pyroelectric properties of Pd—PVDF.

This film, when irradiated by a monochromatic light on both sides, exhibits a thermal interferometic pattern as a photopyroelectric (PPE) effect. FIGS. 1 and 2 illustrate a preferred embodiment of the present invention as a device which produces a fully destructive interferometric (FDI) pattern in the absence of hydrogen gas. The purpose of the fully destructive interferometric (FDI) pattern is to produce no net temperature change in the film over one modulation period and thus no voltage across the metalized electrode surfaces in the absence of hydrogen. In practice, other sources may contribute to a non-zero voltage reading such as background electronic noise due to the extremely low range of the voltage output. The additive presence of hydrogen gas changes the optical absorption characteristics of the film (resulting in signal asymmetry), the ambient gas thermophysical properties (thermal diffusivity and conductivity), and the photothermal electrostatics at the Pd electrode-pyroelectric interface, including unequal work-function exchanges between the two electrode layers. See Wang et al., above and A. Mandelis and C. Christofides, Journal of Applied Physics 70, 4496 (1991). Through changes on the pyroelectric coefficient, which depends on the orientation of macromolecular strings in PVDF (ending in F and H on opposite sides), which defines a net dipole moment across the thickness of the film. The presence of $H^+$ in Pd tends to bias the interface and change the orientation of the molecular strings, thus changing the dipole moment which defines the pyroelectric coefficient. Seeing that the polar signal obtained (AC voltage) across the two electrode surfaces is a product of the pyroelectric coefficient and the pyroelectric oscillating temperature, changes in the pyroelectric coefficient can be used for the ambient $H_2$ sensing principle. The major effect among all the above is the change in the optical absorption coefficient of Pd in the presence of ambient H2.

FIG. 2 is a more detailed cross-section of the sensor probe 6 of FIG. 1.

Light is generated by two lasers 1 (preferably low power, e.g. a few mW, with one possibility being diode lasers) driven by the power supplies 3. The out-of-phase switch 4 is attached to one of the lasers (power supplies) to produce a phase shift ($\Delta\phi$) in one of the light beams. The light is directed via the optical fibers 5 to the gas sensing probe 6 to produce a phase shift ($\Delta\phi$). In a variation, the light source is provided by one laser and a beam splitter. However, there is no limitation on the type, number, and configuration of low power light sources, provided that FDI is produced in the absence of hydrogen gas. A mechanical chopper may be used to modulate the split light beams for the same fixed angular frequency and phase shift. The light sources thus transmitted by the optical fibers (and received at the PVDF film) are preferably modulated at a frequency between about 1 to about 100 Hz, at about the same signal intensity, and out of phase by about 180 degrees.

The radiation from the optical fibers is preferably directed to the opposing surfaces of the photopyroelectric PVDF film 7 (see FIG. 2). In another variation the radiation can be directed to the same side of the pyroelectric film which is partially coated with Pd an Ni-Alloy. The PPE differential signal generated on the PVDF film is preferably collected by a thin wire in an insulating fiber sleeve cable 8, and preferably directed to a preamplifier 9 (see FIG. 1). This PPE signal is then demodulated via the lock-in circuitry 10. The tip of the optical fiber may be locked into a fiberoptic receptacle 11 and may pass through a glass window 12. In one embodiment as shown, the PVDF film is held in place by a teflon ring 13 mounted on the film support 14 which is attached to the chamber 15 (see FIG. 2). The signal baseline is minimized before the introduction of hydrogen gas in the chamber 15 by minimizing optical intensity differences between the two beams impinging on opposite sides of the PVDF film (e.g. adjusting the output/current of one or both lasers). The demodulated signal out of the lock-in circuitry 10 is then stored and sent to an appropriate signal display or processing device 2.

Figure 3:
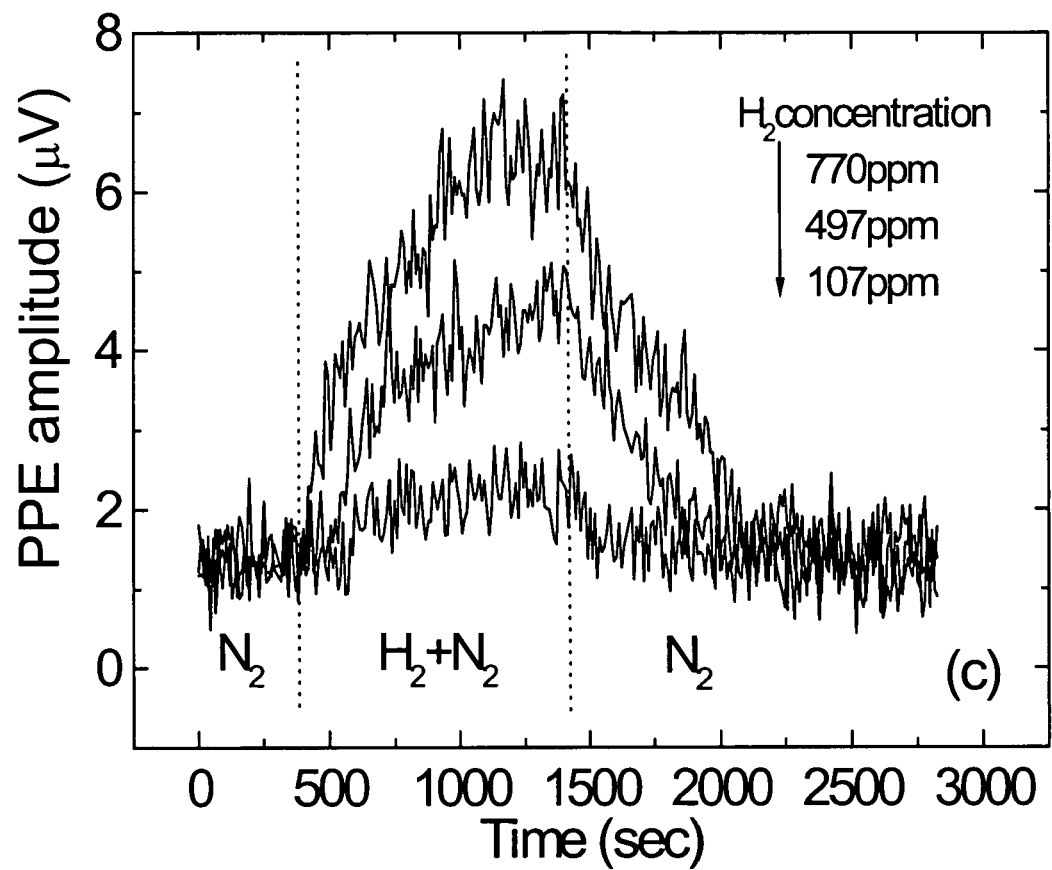
FIG. 3 illustrates a typical PPE signal as a function of time for various concentrations of hydrogen in nitrogen using the PPE interferometric sensor.

As delivered to the PVDF film in the manner outlined above, the light sources produce a fully destructive interferometric pattern in the coated PVDF film in the absence of hydrogen gas. This yields a sensitive differential method of detecting minute changes in the PPE output signal. Baseline suppression provides a high signal-to-noise ratio for the signal detected when hydrogen is present. FIG. 3 illustrates a typical PPE signal as a function of time for various concentrations of hydrogen in nitrogen using the PPE interferometric sensor.

The present invention provides a method for hydrogen gas detection in the concentration range 107 ppm to 100% per volume.

Thermoreflectance Hydrogen Sensing

Figure 4:
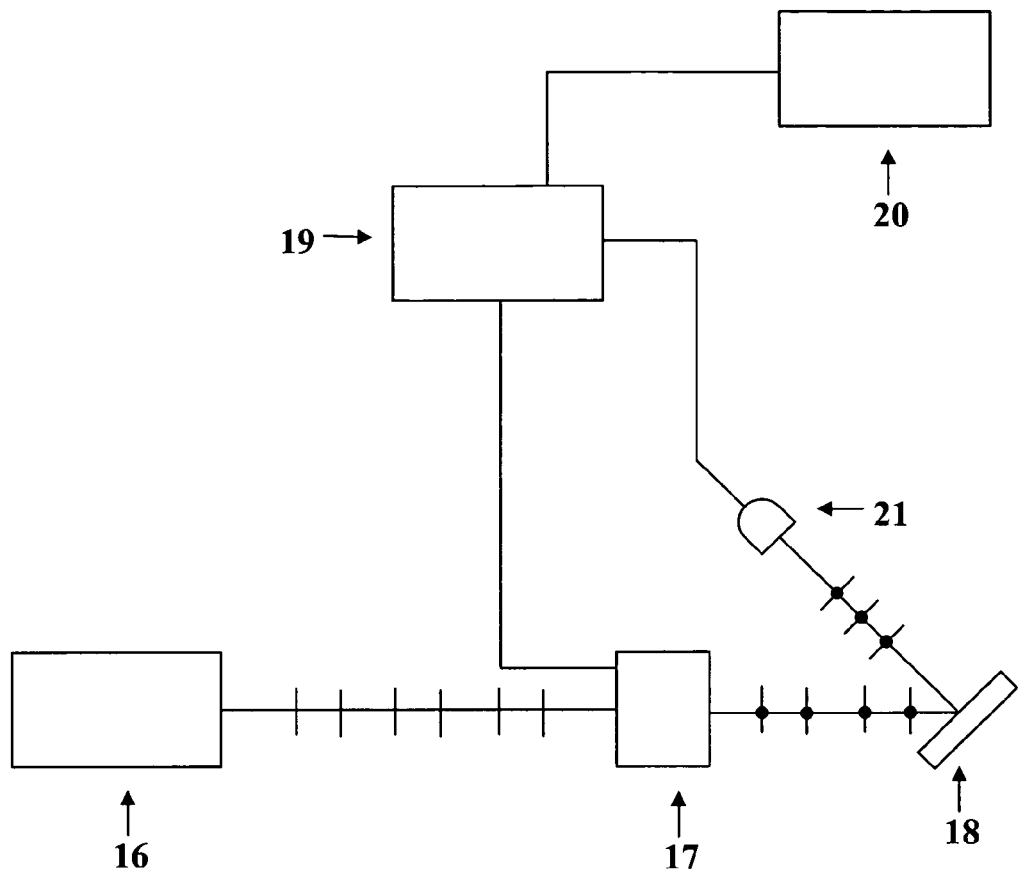
FIG. 4 illustrates a schematic diagram of one embodiment of the invention using differential thermoreflectance with polarization modulation.
Figure 5:
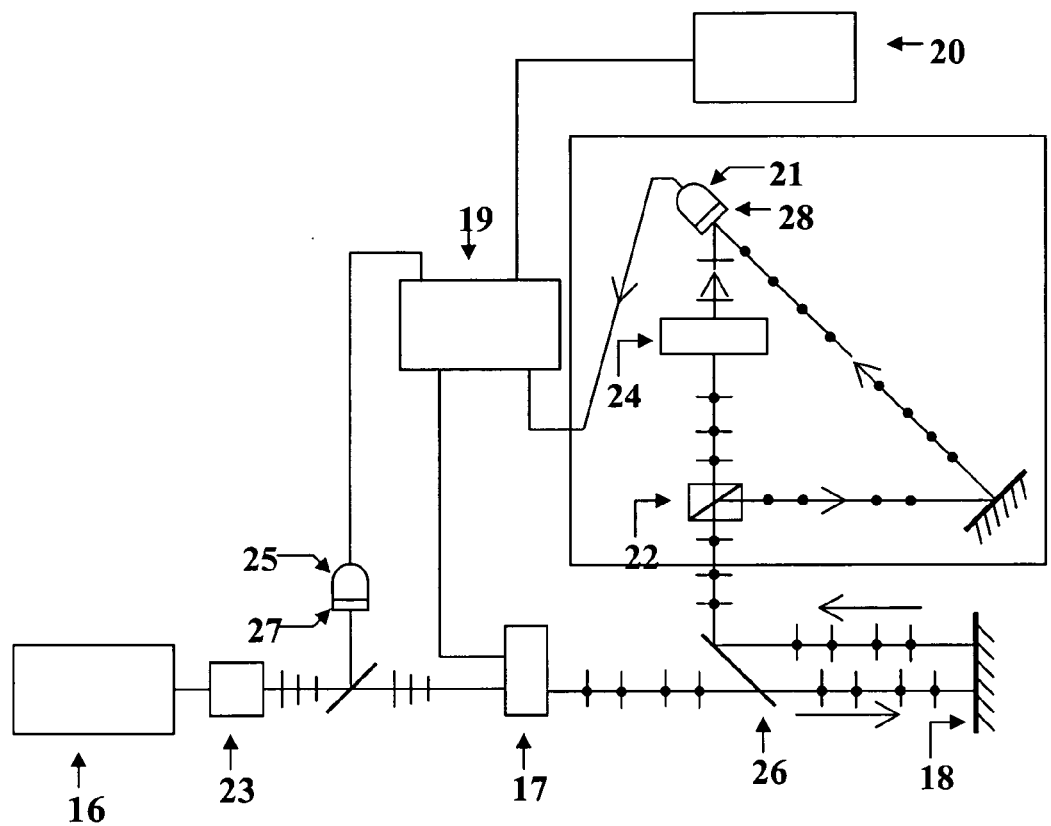
FIG. 5 illustrates a schematic diagram of another embodiment of the invention using differential thermoreflectance with polarization modulation and baseline compensation

As mentioned earlier, surface reflectance and absorptance of Pd vary when exposed to hydrogen, providing further means of detecting the presence of this gas using the orthogonal polarizations of reflected light. A photoelastic modulator 17 (PEM, as shown in FIGS. 4 and 5) is an instrument used for modulating the polarization of a beam of light. A typical example of a PEM 17 widely used is the PEM-90™ of Hinds™ Instruments. The PEM principle of operation is the photoelastic effect. A PEM 17 includes an optical element, such as fused silica, that has attached to it a transducer for vibrating the optical element at a fixed frequency f, within, for example, the low-frequency, ultrasound range of about 20 kHz to 100 kHz. The mass of the element is compressed and extended as a result of the vibration along a modulating axis, imparting oscillating birefringence characteristics into the optical element. The oscillating birefringence on a linear-polarized monochromatic light wave results in variation over time of the phase difference between the orthogonal components of the light that propagates through the optical element. This phase difference is known as retardation or retardance and is typically quantified in terms of waves (e.g. quarter-wave or half-wave). When coherent light is directed via a surface-normal incidence angle through a rectangular optical element, most of that light energy passes through the optical element. In this invention, the retardation is half-wave, as will be clear from the following discussion.

FIG. 4 illustrates one embodiment of the invention using the different reflectivity of orthogonal polarization components of monochromatic polarized light. To obtain differential signals so as to suppress signal baselines that compromise dynamic range of the sensor response, direct a single polarized laser beam (He—Ne or a diode laser will do) from a source 16 incident normal or at an optimal angle on the Pd surface of the sensor film 18 and modulated by a photoelastic modulator 17 (PEM). This results in polarization modulation of the beam. If the incident angle is 90 degrees, a Pellicle beamsplitter 26 (shown in FIG. 5) may be used. The beam is then passed through a rotable sheet polarizer 24, which can change the intensity of the beam and adjusted to create a minimum signal when the exiting beam reaches the photodetector 21 in the absence of ambient hydrogen. The two orthogonal light polarizations ("s" and "p" polarizations) on the Pd surface reflect (and also absorb) differently at different temperatures. When $H_2$ is introduced, its different optical absorption coefficient will increase the temperature of the PVDF film 18 slightly (typically a few hundred millidegrees) and will also change the "s" and "p" polarization reflectances, thus changing the waveform detected by the photodetector. A nonzero differential signal between the two polarization states will be produced. The differential signal can be picked up by using an optical detector 21 such as a photodiode. The detected photoelectric signal is then fed to a lock-in amplifier 19 together with a reference signal at 2 f (twice the frequency f of the PEM 17). Optical fibers are preferably used as the transmission element to guide the light signals, especially where the signal may travel over long distance.

FIG. 5 shows some possible additional features of variations. A beam expander and collimator 23 may be used. A reference signal may be provided by using a beamsplitter 29. The reference signal is directed to a detector 25 through a notch filter 27 to suppress noise from ambient radiation. This detected DC level signal goes into the lock-in ratio input of the lock-in amplifier and results in a real-time signal output which is the ratio of the demodulated AC signal to this reference. The reason for this is that if there is any change to the output intensity of the light source, there would be no change in the signal ratio and false alarms could be eliminated. This ratio can then be fed to a computer 20. The modulated light beam is reflected off the sensor surface 18. As mentioned earlier, if the incident angle of reflection is 90 degrees as shown here, a Pellicle beamsplitter 26 may be used. The reflected light intersects a polarizing beamsplitter 22 such that one polarization passes through undisturbed, while the other polarization is reflected sideways. One of the two split beams should further intersect a rotable sheet polarizer 24, which can change the intensity of the beam as discussed earlier. The two beams will be redirected to meet at the surface of a specialty photodiode detector 21 (which goes along with the PEM 17) with an optional notch filter 28. The rotable sheet polarizer 24 is adjusted to create a minimum detected signal (at the lock-in amplifier 19) upon the overlap of the two beams on the photodetector 21 in the absence of ambient hydrogen.

The polarizing beamsplitter 22 will separate the two polarization components, which will subsequently be reunited after adjusting the intensity of one of them, so that the (ideally) square reflected waveform of each half cycle will precisely meet the same level of square reflected waveform of the other half cycle to generate a continuous signal over one period upon recombination at the detector (photodiode). (However, that this separation of the polarizations would not be necessary is shown in the embodiment illustrated in FIG. 4.)

Consequently, during 50 percent of the modulation period, the detector 21 receives a wave that has a given signal. During the remaining 50%, another wave arrives (associated with the other polarization), that has the same amplitude. Therefore, there is no difference in signal level to the detector 21; a signal level resembling a DC signal (continuous line with no dips or bumps) is incident on the lock-in amplifier 19 which then outputs a zero signal (provided the two beams are ideally square), of zero risetime compared to the repetition period of the waveform, and of ideal half-cycle duration each (depending on the PEM 17).

The basic detection principle is that one of the two polarizations will be affected more by the presence of hydrogen gas; and a tiny bump or dip will appear as a signal from the detector after the 50% of the modulation cycle (first half of the wave) has elapsed. The size of the bump or dip will depend on the value of the absorption (and thus reflection) coefficient of Pd at that concentration, so this is the dependence of the output signal on the concentration of hydrogen gas. In summary, the Pd-film temperature increase due to the $H_2$ absorption and increase in the optical absorption coefficient, the "s" and "p" polarization reflectances will vary.

Figure 6:
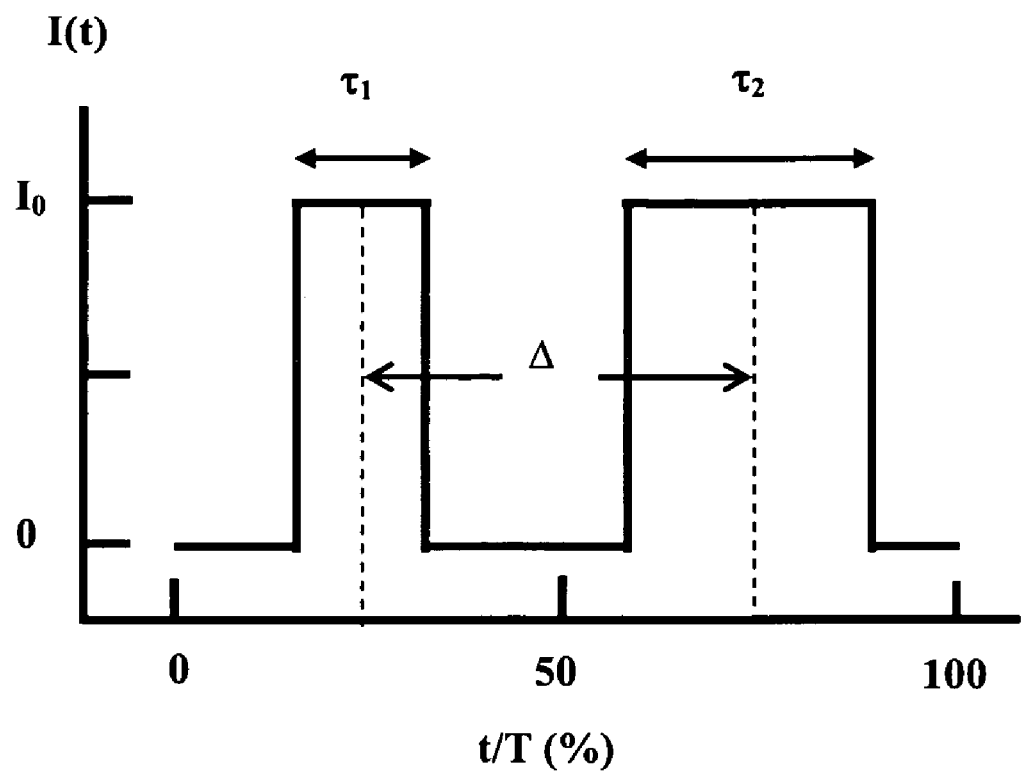
FIG. 6 illustrates a two-pulse repetitive waveform for a common-mode rejection waveform.

In a further embodiment, the differential signal may be further optimized by using a common-mode rejection waveform, such as described in A. Mandelis, S. Paoloni and L. Nicolaides, Rev. Sci. Instrum. 71 (8), 2440–2444 (June 2000), S. Paoloni, L. Nicolaides and A. Mandelis, Rev. Sci. Instrum. 71 (8), 2445–2451 (June 2000), and U.S. patent application Ser. No. 09/813,357. This can be done by using an acousto-optic modulator to chop the laser beam and impose on it a dual waveform, which suppresses the lock-in signal baseline and can be zeroed at zero $H_2$ concentration. This combination of techniques (with the special waveform) is that the zero of the signal will occur when the area under the first transient pulse (under the first square wave) is subtracted from that of the second pulse (second square wave). The zero can be set by scanning the separation time at $[H_2]=0$. Under a non-zero hydrogen ambient, the changed optical absorption coefficient will change the temporal shape of the two pulses, thus yielding a net non-zero lock-in output. A typical two-pulse repetitive waveform is shown in FIG. 6.

In a variation, that the combination of changes in reflectance (optical part) and absorptance (i.e. conversion to heat; thermal part) would reinforce each other can be used for hydrogen gas detection. As the reflectance depends on polarization, so would the absorptance (complementary to reflectance in energy terms); so modulating the polarization will yield two simultaneous and useful signals: one signal will be purely optical (change in reflectance) and would be monitored with a photodiode; another signal would be photothermal (change in absorptance) and monitored by the pyroelectric effect on the palladianized sensor. This would be a hybrid version of the differential thermoreflectance or thermoabsorptance methods of hydrogen sensing, using aspects as described above.

It will be appreciated by those skilled in the art that numerous other configurations for generating and measuring the resulting PPE signal may be used. For example other pyroelectric materials (i.e. ceramics) can be used and types (various wavelenghts) of optical excitation sources. Also, other photoreflecting materials than palladium and PVDF may be used for the thermoreflectance hydrogen sensing provided that the reflectances of the polarizations are affected differently. The above examples are meant to be non limiting and illustrative only.

While this hydrogen sensor has been described and illustrated with respect to embodiments of particular hardware arrangements, it will be appreciated that numerous variations of the apparatus components and methodologies may be made without departing from the scope of this invention.

All patents, patent applications, and publications, if any, referred to are incorporated by reference in their entirety.

Therefore what is claimed is:

1. An apparatus for detecting hydrogen gas comprising:
a radiation source for generating at least two optical signals of about the same modulation frequency;
a sensor head, comprising a pyroelectric film, the pyroelectric film including a first side coated with a hydrogen-sensitive metallic substance and a second side with a hydrogen insensitive metallic substance;
said sensor head, comprising a pyroelectric film with a hydrogen-sensitive side, which is further overcoated with a protective coating preventing the said hydrogen sensitive metallic substance from becoming poisoned due to prolonged exposure to ambient pollutants;
a remote optical signal transmission element for delivering from the radiation source an optical signal to the first side and an optical signal to the second side, thereby generating an essentially zero voltage or signal base line suppression across the two sides in the absence of hydrogen gas and a non-zero differential voltage in the presence of hydrogen gas;
circuit element to generate the modulated optical excitation and detect the modulated generated differential signal;
circuit element electronically connected to the two sides for monitoring the modulated voltage and demodulating said differential signals; and
outputting said demodulated differential signals and storing said demodulated differential signals or displaying said demodulated differential signals.

2. The apparatus of claim 1, wherein the said modulated optical signal is a coherent light wave, and the second of the said modulated optical signal is a coherent light wave of about the same intensity as the first said optical signal and about 180 degrees out of phase relative to the first said optical signal; the intensity difference between the said optical signals is minimized through appropriate adjustment with an optical transmission element or a polarizer placed in the path of one or the other coherent wave.

3. An apparatus for detecting hydrogen gas comprising:
a radiation source for generating a monochromatic optical signal;
a photoelastic modulator for modulating the polarization of the optical signal;
a sensor head, comprising a photoreflecting film, the photoreflecting film including a sensor surface coated with a photoreflecting metallic substance;
a first optical signal transmission element for delivering from the radiation source the optical signal to the sensor surface;
a photodetector for converting the optical signal reflected off the sensor to a photoelectric signal; and
circuit element electronically connected to the photodetector for monitoring the photoelectric signal generated.

4. The method according to claim 1 or 2 wherein the said radiation source is a solid state diode laser.

5. The method according to claim 1, wherein the wavelength of said diode laser can be in the UV, infrared or visible range.

6. The method according to claim 1 or 2 wherein the radiation source is a light emitting diode (LED).

7. The method according to claim 1 or 2 wherein the generating of two synchronous-modulated out of phase (180 degrees) optical excitation signals is done by using two modulated laser diode power supplies and two solid state diode lasers.

8. The method according to claim 1 or 2 wherein the generating of two synchronous-modulated out of phase (180 degrees) optical excitation signals is done by using a single modulated laser diode power supply, two solid state diode lasers and appropriate phase shifting switch.

9. The method according to claim 1 or 2 wherein the generating of said synchronous-modulated out of phase (180 degrees) optical excitation signals is done by using a compact integrated electronic circuit that includes laser intensity modulation, phase shifting and PPE signal demodulation.

10. The method according to claim 1 or 2 wherein said modulation of optical excitation signals is done by using current modulation of the diode laser.

11. The method according to claim 1 or 2 wherein said modulation of optical excitation signals is done by using an external modulation means of the diode laser such as a mechanical chopper.

12. The method according to claim 1 wherein said pyroelectric film in the gas sensing enclosure is a Polyvinylidene (di)fluoride (PVDF) thin film.

13. The method according to claim 1 wherein said pyroelectric film is made of ceramic material (PZT, LiNbO3, or LiTaO3; this list is not all inclusive).

14. The method according to claim 1, 12, or 13 wherein said pyroelectric film is coated on one side with Pd as the hydrogen-sensitive metallic substance protected with an organic or inorganic film for high stability and a second side coated with a hydrogen insensitive metallic substance.

15. The method according to claim 1 wherein delivering the irradiation from the said irradiation source to the said gas sensing head is done by optical fibers.

16. The method according to claim 1 wherein delivering the irradiation from the said irradiation source to the gas sensing head is done directly to the pyroelectric film.

17. The method according to claim 1 wherein said modulating of the optical excitation and demodulating of the generated signal is done by using an electronic lock-in circuit.

18. The method according to claim 1 wherein said demodulated signals is outputted, stored or displayed by electronic means.

19. The method according to claim 3 wherein the said radiation source is a solid state diode laser.

20. The method according to claim 3 or 19 wherein the wavelength of said diode laser can be in the UV, infrared or visible range.

21. The method according to claim 3 wherein the radiation source is a light emitting diode (LED).

22. The method according to claim 3 or 19 wherein said polarization modulation is done by a photoelastic modulator; the reflected beam is at an optimal incidence angle or normal to the surface of the active element and the presence of absorbed hydrogen generates an asymmetric reflection in the two orthogonal polarizations of the reflected beam.

23. The method of claim 22 wherein the reflected beam is intercepted by a photodiode connected to a lock-in amplifier referenced at twice the frequency of polarization modulation.

24. The method of claim 21 wherein a baseline adjustment of a normally reflected beam at zero hydrogen concentration is effected by splitting apart the two polarization components and using (rotating) a polarizer to equalize their intensity at the photodiode.

25. The method according to claim 3 or 19 wherein said photoreflecting film, includes a sensor surface coated with a highly stable hydrogen-sensitive photoreflecting metallic substance such as palladium.

26. The method according to claim 3 or 19 wherein said photoreflecting film is a pyroelectric polymer such as PVDF.

27. The method according to claim 3 or 19 wherein said photoreflecting film is made of pyroelectric ceramic material (i.e. PZT, LiNbO3 or LiTaO3; this list is not all inclusive).

28. The method according to claim 3 or 19 wherein said delivering of the irradiation from the excitation optical sources to the gas sensing probe is done by optical fiber.

29. The method according to claim 3 or 19 wherein said delivering of the irradiation from the excitation optical sources to the gas sensing probe is done directly onto the pyroelectric film.

30. The method according to claim 3 or 19 wherein said photodetector (photodiode) converts the optical signal reflected off the sensor surface to an electric signal.

31. The method according to claim 3 or 19 wherein said monitoring of the photoelectric signal is done by using a lock-in circuit element.

32. The method according to claim 3 wherein said demodulated signals is outputted, stored or displayed by electronic means.

33. The method according to claim 1 wherein said signal baseline suppression is effected by implementing the Common-Mode Rejection Demodulation waveform using an acousto-optic modulator and single-ended laser beam incidence on the said hydrogen-sensitive metallic substance.

* * * * *